US011903909B2

(12) United States Patent
Igumnov et al.

(10) Patent No.: US 11,903,909 B2
(45) Date of Patent: Feb. 20, 2024

(54) COMBINED LIPOSUCTION METHOD

(71) Applicants: Limited Liability Company "Center for Plastic Surgery and Cosmetology "Sharm"", Novosibirsk (RU); Vitaly Alexandrovich Igumnov, Novosibirskaya Oblast (RU); Alexandr Alexandrovich Igumnov, Novosibirskaya Oblast (RU)

(72) Inventors: Vitaly Alexandrovich Igumnov, Novosibirskaia Oblas (RU); Alexandr Alexandrovich Igumnov, Novosibirskaia Oblas (RU)

(73) Assignees: LIMITED LIABILITY COMPANY "CENTER FOR PLASTIC SURGERY AND COSMETOLOGY "SHARM"", Novosibirsk (RU); VITALY ALEXANDROVICH IGUMNOV, Novosibirskaya Oblast (RU); ALEXANDR ALEXANDROVICH IGUMNOV, Novosibirskaya Oblast (RU)

( * ) Notice: Subject to any disclaimer, the term of this patent is extended or adjusted under 35 U.S.C. 154(b) by 1121 days.

(21) Appl. No.: 16/588,170

(22) Filed: Sep. 30, 2019

(65) Prior Publication Data
US 2020/0101206 A1 Apr. 2, 2020

(30) Foreign Application Priority Data
Oct. 1, 2018 (RU) .................................. 2018134622

(51) Int. Cl.
A61K 31/137 (2006.01)
A61B 18/22 (2006.01)
A61K 9/00 (2006.01)
A61K 9/08 (2006.01)
A61K 31/167 (2006.01)
A61K 47/02 (2006.01)
A61B 18/00 (2006.01)
A61B 18/20 (2006.01)
A61M 1/00 (2006.01)

(52) U.S. Cl.
CPC ............ *A61K 31/137* (2013.01); *A61B 18/22* (2013.01); *A61K 9/0019* (2013.01); *A61K 9/08* (2013.01); *A61K 31/167* (2013.01); *A61K 47/02* (2013.01); *A61B 2018/00464* (2013.01); *A61B 2018/00761* (2013.01); *A61B 2018/00839* (2013.01); *A61B 2018/2005* (2013.01); *A61B 2018/2205* (2013.01); *A61M 1/89* (2021.05); *A61M 2202/048* (2013.01); *A61M 2202/08* (2013.01)

(58) Field of Classification Search
CPC . A61B 2018/00464; A61B 1/89; A61B 1/892; A61B 1/893; A61B 1/895
See application file for complete search history.

(56) References Cited

U.S. PATENT DOCUMENTS

| 8,974,442 B1* | 3/2015 | Boss, Jr. | ............... A61B 18/203 606/2 |
| 2007/0208366 A1* | 9/2007 | Pellegrino | ............. A61M 29/02 606/198 |
| 2012/0022510 A1* | 1/2012 | Welches | ................. A61B 18/22 606/14 |

OTHER PUBLICATIONS

DiBernardo BE, Reyes J. Evaluation of skin tightening after laser-assisted liposuction. Aesthet Surg J. Sep. 2009-Oct. 29(5):400-7. doi: 10.1016/j.asj.2009.08.006. PMID: 19825469. (Year: 2009).*
Alexiades, M. (2016). Combination Laser-Assisted Liposuction and Minimally Invasive Skin Tightening with Temperature Feedback for Treatment of the Submentum and Neck. In: Shiffman, M., Di Giuseppe, A. (eds) Liposuction. Springer, Berlin, Heidelberg. https://doi.org/10.1007/978-3-662-48903-1_35 (Year: 2016).*
Shiffman, M.A. (2016). Tumescent Technique. In: Shiffman, M., Di Giuseppe, A. (eds) Liposuction. Springer, Berlin, Heidelberg. https://doi.org/10.1007/978-3-662-48903-1_2 (Year: 2016).*
Schavelzon, D.E., Blugerman, G., Chomyszyn, A. (2016). Laserlipolysis. In: Shiffman, M., Di Giuseppe, A. (eds) Liposuction. Springer, Berlin, Heidelberg. https://doi.org/10.1007/978-3-662-48903-1_34 (Year: 2016).*
Kim, S.W., Kim, Y.H. (2016). Analysis of Postoperative Complications of Superficial Liposuction. In: Shiffman, M., Di Giuseppe, A. (eds) Liposuction. Springer, Berlin, Heidelberg. https://doi.org/10.1007/978-3-662-48903-1_80 (Year: 2016).*
Newman, J., R. L. Dolsky, and S. T. Mai. "Submental Liposuction Extraction With Hard Chin Augmentation." Archives of otolaryngology—head & neck surgery 110.7 (1984): 454-457. Web. (Year: 1984).*
DiBernardo BE, Reyes J. Evaluation of skin tightening after laser-assisted liposuction. Aesthet Surg J. Sep.-Oct. 2009;29(5):400-7. doi: 10.1016/j.asj.2009.08.006. PMID: 19825469. (Year: 2009).*
Chia, Christopher T., and Spero J. Theodorou. "1,000 Consecutive Cases of Laser-Assisted Liposuction and Suction-Assisted Lipectomy Managed With Local Anesthesia." Aesthetic plastic surgery 36.4 (2012): 795-802. Web. (Year: 2012).*

(Continued)

*Primary Examiner* — Catharine L Anderson
*Assistant Examiner* — Arjuna P Chatrathi
(74) *Attorney, Agent, or Firm* — Muncy, Geissler, Olds & Lowe, P.C.

(57) ABSTRACT

The invention relates to combined liposuction methods and can be used in surgical interventions to remove local fat deposits in the lower third of the face and neck. The method includes a preoperative examination of the patient when one or more areas of the lower third of the face and neck of the patient are designated as liposuction areas constituting the operative field. The contour boundaries of the operative field and at least one operative access point are determined. Uniform infiltration anesthesia of the adipose tissue to be removed in the liposuction areas is performed. From a Nd:YAG laser radiation source with a wavelength of 1064 nm, a Nd:YAG laser radiation with a wavelength of 1064 nm in a pulsed mode with a frequency of 50 Hz, with a pulse duration of 300 μs and a power of the predetermined value is supplied directly to the adipose tissue to be removed.

23 Claims, No Drawings

(56) References Cited

OTHER PUBLICATIONS

DeFatta, Robert, and Yadranko Ducic. "Liposuction of the Face and Neck." Operative techniques in otolaryngology—head and neck surgery 18.3 (2007): 261-266. Web. (Year: 2007).*

Bergfeld, D., Sommer, B., Sattler, G. (2001). Infiltration Technique. In: Hanke, C.W., Sommer, B., Sattler, G. (eds) Tumescent Local Anesthesia. Springer, Berlin, Heidelberg. https://doi.org/10.1007/978-3-642-56744-5_9 (Year: 2001).*

Bergfeld, D., Sommer, B. (2001). Patient Selection and Preoperative Preparation. In: Hanke, C.W., Sommer, B., Sattler, G. (eds) Tumescent Local Anesthesia. Springer, Berlin, Heidelberg. https://doi.org/10.1007/978-3-642-56744-5_11 (Year: 2001).*

\* cited by examiner

COMBINED LIPOSUCTION METHOD

The invention relates to the field of medicine, namely to combined liposuction methods, and can be used in cosmetic surgery to remove local fat deposits that deform the contours of the lower third of the face and neck of the patient.

For many patients who visit an aesthetic surgeon, the most urgent problem is the correction of gravitational changes in the lower third of the face, which is often accompanied by the presence of excess body fat in the submental (under the chin) and lower neck areas, up to the level of the jugular notch. At the same time, when choosing methods for eliminating fat deposits in the areas of the lower third of the face and neck, patients make high demands on the quality of corrective procedures and the resulting effect, as well as strive for a minimal risk of postoperative complications and a minimum period of postoperative recovery, due to the dynamic life rhythm of potential patients. Reasonably high-efficient way to remove local fat deposits in the lower third of the face and neck is liposuction using laser radiation, which, in comparison with traditional liposuction methods, has several advantages. These include skin retraction due to the formation of new collagen, a decrease in intraoperative and postoperative bleeding, as well as reduction of adipocyte population. When performing laser liposuction, the energy of laser radiation, which is supplied directly to adipose tissue (i.e., acts on the tissue by contact method), is absorbed by adipocytes and converted into thermal energy, thereby causing a local temperature increase in the adipose tissue to be removed. In turn, heat acts on adipocytes, the content of adipocytes expands, and their membranes are destroyed. Thus, there is a thermal effect in the adipose tissue resulting from the laser radiation exposure, which leads to lipodestruction. The intercellular substance and capillaries also undergo thermal degradation. Laser lipolysis, in addition to the manifestation of the thermal effect, can also be accompanied by wave effects that occur in the adipose tissue to be removed. This is, in particular, the photoacoustic effect that occurs due to the rapid absorption and heating of fat cells under the action of laser radiation and may also be important for the course of the lipolysis process, as well as the shock-wave effect that can occur due to the action of a focused powerful laser beam and become a cause of mechanical damage to adjacent tissues. The process of absorption of laser energy by a tissue is due to the ability of the tissue to absorb wave energy and largely depends on the wavelength of the laser radiation. So, for laser lipolysis, including the areas of the lower third of the face and neck, laser radiation from a source of yttrium-aluminum garnet with neodymium (Nd:YAG laser radiation) with a wavelength of 1064 nm is used, since it is absorbed by lipids quite strongly to ensure penetration into adipose tissue. At the same time, since Nd:YAG laser radiation with a wavelength of 1064 nm is sufficiently selective for lipids, it does not have an undesirable thermal effect on tissues adjacent to fat, and thereby contributes to less traumatization and faster repair of the treated area. At the same time, Nd:YAG laser radiation with a wavelength of 1064 nm affects the collagen most intensively, which provides the best result in skin tightening and stimulates neocollagenesis. The absorption of this wavelength by hemoglobin eliminates bleeding during surgery, as well as provides a short recovery period without severe lymphorrhea. Thus, the determination of the wavelength of laser radiation for laser lipolysis, including areas of the lower third of the face and neck, is theoretically justified and in practice does not cause difficulties. However, the effects (thermal, shock-wave, and others) obtained as a result of the action of laser radiation on the target tissue are determined not so much by the wavelength of the laser radiation as the degree to which the energy of laser radiation with a certain wavelength is absorbed and transformed into heat in this target tissue. In turn, this factor of interaction of the target tissue with laser radiation depends on the energy and time parameters of the laser radiation, as well as the biological and physicochemical properties of the target tissue itself, and to a large extent, on thermal conductivity and thermal relaxation time thereof, i.e., the time during which the target tissue dissipates 63% of the heat in the surrounding tissue structures. As for the energy and time parameters of laser radiation, the effects resulting from the action of laser radiation with a specific wavelength on the target tissue depend on the amount of energy (J) absorbed by a certain volume of tissue and on the distribution of absorbed energy by the area of its flow (i.e., by the energy flow density, J/cm 2) and by time, which, in turn, is determined by the flow rate (i.e., power) of energy (W), duration (s) and frequency (Hz) of laser exposure of the irradiated target tissue per time unit. Thus, the determination of the optimal energy and timing parameters of laser radiation of a certain wavelength during the liposuction operation is of great importance in order to provide a destructive effect on the adipose tissue to be removed, which is proper to the most complete lipodestruction of its entire volume in the treated area of the patient's body and, at the same time, to minimize the likelihood of unwanted traumatization to tissue structures adjacent to adipose tissue and, thus, ensure a high aesthetic effect and reduce the postoperative recovery period following liposuction.

From the description of patent RU 264762 (published 16 Mar. 2018), a combined liposuction method is known that is selected as the closest analogue of the claimed invention, which method can be used in cosmetic surgery during surgical interventions to remove local fat deposits that deform the contours of the lower third of the face. According to the known combined liposuction method, the closest analogue, a preoperative examination of the patient is carried out, the contour boundaries of the operative field are applied in the areas of the lower third of the face and neck when the patient is standing, and the location of the operative approach point is chosen in the area of the submental fold. The required amount of anesthetic support is used, depends on the amount of fat removed. Transcutaneous skin punctures are made along the contour boundaries of the operative field, as well as at the selected operative approach points, and a tumescent solution is administered through them into the adipose tissue to be removed to ensure local intracellular hyperhydration of adipocytes, thus ensuring uniform infiltration of the adipose tissue to be removed. After sufficient time for the onset of vasoconstriction, the adipose tissue to be removed is destructively exposed to Nd:YAG laser radiation with a wavelength of 1064 nm, which is supplied directly to the adipose tissue to be removed through an fiber optic light guide with a fiber thickness of 600 microns. To do this, the first end of the fiber optic light guide is connected to a source of the Nd:YAG laser radiation with a wavelength of 1064 nm, and the second, emitting end of the fiber optic light guide is inserted into an optical cannula to allow it to be inserted into the adipose tissue to be removed. An optical cannula with the fiber optic light guide placed in it is inserted into the adipose tissue to be removed through a transcutaneous puncture of the skin at the selected operative approach point in the sub-mental fold and is put forward by continuous in and out movements over the entire area and depth of the treated area of the operative field, with the optical cannula approaching to the front surface of the lower jaw. The formed emulsified adipocyte fat detritus is removed from the liposuction area through an aspiration cannula, after which the dermis in the liposuction area is heated to 39-40° C. using Nd:YAG laser radiation with a wavelength of 1064 nm, which is supplied from the laser radiation source of the said radiation to the liposuction area via the fiber optic light guide. At the end of the operation, aseptic and compression dressings are applied and the postoperative period is performed. In the known combined liposuction method, Nd:YAG laser radiation with a wavelength of 1064 nm is used for the destruction of adipose tissue. This ensures the absorption of the acting radiation energy by the adipose tissue to be removed and, as a result, heating thereof. The use of Nd:YAG laser radiation with a wavelength of 1064 nm also allows stimulation of neocollagenesis and reduces the likelihood of bleeding during liposuction surgery in a known manner. However, the combined liposuction method, the closest analogue, is not reliable enough to obtain a high aesthetic effect and a short recovery period following liposuction. This is due to the fact that in the known combined liposuction method, the energy and time parameters of laser radiation affecting the adipose tissue to be removed are not determined. In this regard, there is a high probability that when performing the known combined liposuction method, the laser exposure of the adipose tissue to be removed will not be proper to provide a thermal effect within the entire volume of the adipose tissue to be removed. Therefore, adipose tissue will not be completely removed from the treated operative field, due to which, a sufficiently high aesthetic effect as a result of liposuction will not be achieved. There is also the possibility of excessively rapid heating of adipose tissue following the supply of high-density energy thereto, which can lead to the traumatization to tissue structures adjacent to adipose tissue and, as a result, to a relatively long recovery period and, with a high probability, to a deterioration of the final aesthetic effect. In addition, the known combined liposuction method suggests the possibility of performing liposuction only in the areas of the lower jaw and the submental area of the neck, but does not allow liposuction in the areas of the neck located below its submental area, right down to the jugular notch. Thus, the known combined liposuction method does not allow to provide an aesthetically more harmonious effect in the case where excess fat deposits are present not only in the submental, but also in other underlying areas of the patient's neck.

The claimed invention is directed at solving the problems of increasing the reliability of the combined liposuction method to obtain a high aesthetic effect and a short recovery period as a result of the liposuction operation, to obtain a harmonious aesthetic effect as a result of the liposuction operation, as well as to expand the range of tools for similar purposes.

These problems are solved by the fact that in the combined liposuction method, which comprises performing a preoperative examination of the patient, planning an operation, wherein one or more areas of the lower third of the face and neck of the patient from a number of such as the submental area of the neck, the lower jaw areas, the neck area from the submental area to the level of the cricoid cartilage, and the neck area from the submental area to the level of the jugular notch, are designated as liposuction areas constituting the operative field, wherein the contour boundaries of the operative field and at least one operative approach point are determined, performing uniform infiltration anesthesia of the adipose tissue to be removed in the liposuction areas, using an Nd:YAG laser radiation source with a wavelength of 1064 nm and a fiber optic light guide with a fiber thickness of 600 microns, with the first end of the fiber optic light guide optically connected to the said laser radiation source, and the second end of the fiber optic light guide made with an emitting radiation surface and providing the possibility of insertion thereof into the adipose tissue to be removed through transcutaneous punctures of skin, causing the destructive effect on the adipose tissue to be removed by Nd:YAG laser radiation with a wavelength of 1064 nm, which is supplied in a pulsed mode with a frequency of 50 Hz, with a pulse duration of 300 µs and a power of the predetermined value from the laser radiation source of the said radiation through the fiber optic light guide directly to the adipose tissue to be removed in the liposuction areas, for which the second end of the fiber optic light guide is inserted into the adipose tissue to be removed through transcutaneous skin punctures at predetermined operative approach points and put forward by continuous in and out movements within the volume of the adipose tissue to be removed to ensure uniform destruction of the latter over the entire area and depth of the treated liposuction area, removal of the formed emulsified adipocyte fat detritus from the liposuction areas, closing the surgical wounds with aseptic dressings at the end of the operation, applying of compression dressing on the liposuction area, and performing the postoperative period, wherein in the case where operative field is the submental area of the neck, the Nd:YAG laser radiation power with a wavelength of 1064 nm is set in the range from 8 W to 12 W, in the case where the operative field is the submental area of the neck and the lower jaw areas, the Nd:YAG laser radiation power with a wavelength of 1064 nm is set in the range from 12 W to 14 W, in the case where the operative field consists of the submental area of the neck, the lower jaw areas, and the neck area from the submental area to the level of the cricoid cartilage, the Nd:YAG laser radiation power with a wavelength of 1064 nm is set in the range from 14 W to 15 W, in the case where the operative field consists of the submental area of the neck, the lower jaw areas, and the neck area from the submental area to the level of the jugular notch, the Nd:YAG laser radiation power with a wavelength of 1064 nm is set in the range from 15 W to 16 W.

In contrast to the known combined liposuction method, the closest analogue, the claimed invention comprises the inclusion in the operative field neck areas underlying from the submental area, namely, the neck area from the submental area to the level of the cricoid cartilage, and the neck area from the submental area to the jugular notch. Moreover, the claimed combination of essential features of the combined liposuction method determines the energy and time parameters of exposure of the adipose tissue to be removed to Nd:YAG laser radiation with a wavelength of 1064 nm, which, together with other essential features of the claimed invention, provide the degree of absorption and distribution of radiation energy in the adipose tissue to be removed, which is optimal to provide a thermal effect within the entire volume of the adipose tissue to be removed and, at the same time, reduces the likelihood of undesirable traumatization effects. Whereby the aforementioned thermal effect and a decrease in the likelihood of undesirable traumatization effects can be provided within the volumes of the adipose tissue to be removed located both in the areas of the lower jaw and in all areas throughout the neck, since the mentioned parameters of the laser action on the adipose tissue to be removed are determined for various practical cases of inclusion of certain areas of the lower third of the face and neck in the operative field to remove adipose tissue therein. Thus, this provides a destructive effect on the adipose tissue to be removed, proper to the most complete lipodestruction of its entire volume in the lower third of the face and in all areas of the patient's neck and, at the same time, reduces the likelihood of unwanted traumatization to tissues in the liposuction areas, which is a technical result of the claimed combined liposuction method. This increases the reliability of the combined liposuction method to obtain a high aesthetic effect and a short recovery period, and also provides a more harmonious aesthetic effect as a result of liposuction operation. Also, the implementation of the claimed combined liposuction method will expand the range of tools for similar purposes.

In the combined liposuction method, a preoperative examination of a patient includes taking patient's history, determining the patient's indications and contraindications for surgery, conducting laboratory tests for biochemical and general blood analysis, determining the blood group, Rh factor, Wasserman reaction, detecting antibodies to HIV, blood testing for hepatitis, doing an electrocardiogram of the patient, as well as examining by a therapist. In this case, a biochemical blood test includes the determination of indicators for bilirubin, aminotransferase AST and ALT, sugar, creatinine, protein, electrolytes, and blood lipids.

In the combined liposuction method, operation planning may include photographing the areas of liposuction in several projections. This allows a visual assessment of the aesthetic effect obtained as a result of the liposuction operation, in comparison with the initial state of the treated areas of the lower third of the face and neck of the patient.

In the combined liposuction method, uniform infiltration anesthesia of the adipose tissue to be removed is performed by injecting infiltrating anesthetic fluid therein under pressure through transcutaneous skin punctures to provide local intracellular hyperhydration of adipocytes. At the same time, transcutaneous skin punctures are made along the contour boundaries of the operative field, and at least a portion of transcutaneous skin punctures are located at all predetermined operative approach points. In this case, the infiltrating anesthetic liquid is administered into the adipose tissue to be removed using, for example, standard syringes.

In the combined liposuction method, a tumescent solution is used as an infiltrating anesthetic liquid, which contains 50 ml of a 1% solution of lidocaine hydrochloride, 1 ml of adrenaline, 12.5 ml of an 8.4% sodium bicarbonate solution and physiological saline in the form of 0.9% aqueous NaCl solution in an amount of up to 1000 ml, while the ratio of the volume of the tumescent solution to the volume of adipose tissue to be infiltrated is from 1:1 to 3:1, respectively.

In the combined liposuction method, an optical cannula is used to provide possibility to insert the second end of the fiber optic light guide into the adipose tissue to be removed through transcutaneous skin punctures, while the second end of the fiber optic light guide is placed inside the cannula so that emitting radiation surface thereof is able to emit radiation outside the optical cannula.

In the combined liposuction method, for performing liposuction in the submental area of the neck and the lower jaw areas, single operative approach point is determined in the area of the submental fold, wherein in and out movements of the second end of the fiber optic light guide within the volume of the adipose tissue to be removed are performed by entering into the front surface of the lower jaw.

In the combined liposuction method, for performing liposuction in the neck area from the submental area to the level of the cricoid cartilage or to the level of the jugular notch, it is preferable to determine two operative approach points, wherein their location is determined under the corners of the lower jaw, by one operative approach point from each side of the neck.

In the combined liposuction method, after performing uniform infiltration anesthesia of the adipose tissue to be removed and before the applying destructive effect to the adipose tissue to be removed using Nd:YAG laser radiation with a wavelength of 1064 nm, tunnels can be formed in the adipose tissue to be removed, for which purpose a cannula is inserted through transcutaneous skin punctures at predetermined operative approach points into the adipose tissue to be removed, and then the cannula is put forward by in and out movements within the entire volume of the adipose tissue to be removed, wherein the tunnels are formed close to each other, for example, in the form of a fan-shaped network, and after the second end of the fiber optic light guide is inserted into the adipose tissue to be removed, the fiber optic light guide is put forward by continuous in and out movements inside each tunnel formed within the volume of the adipose tissue to be removed.

In the combined liposuction method, transcutaneous skin punctures are expanded with a blunt dilator for insertion of the second end of the fiber optic light guide or cannula therein.

In the combined liposuction method, when applying the destructive effect to the adipose tissue to be removed, the second end of the fiber optic light guide is put forward within the volume of the adipose tissue to be removed, starting from lower layers of adipose tissue with the subsequent transition to overlying layers thereof, which is preferable to ensure uniform destruction of the adipose tissue to be removed throughout the entire depth of the treated area in the operative field.

In the combined liposuction method, the removal of the formed emulsified adipocyte fat detritus from the liposuction area is performed by means of an aspiration cannula using a negative pressure of 0.2-0.3 bar.

In the combined liposuction method, after removal of the formed emulsified adipocyte fat detritus from the liposuction areas, the dermis therein is heated to 39-40° C. by Nd:YAG laser radiation with a wavelength of 1064 nm, which is supplied from the source of said radiation to the liposuction area through the fiber optic light guide.

Heating the dermis to 39-40° C. allows even tightening of the skin in the affected area, increasing its turgor, thereby further enhancing the aesthetic effect resulting from the liposuction operation.

In the combined liposuction method, during the postoperative period, surgical wounds are ligated using antiseptic solutions and water-soluble ointments with simultaneous administration of medications and antibacterial therapy with broad-spectrum antibiotics for 5-7 days after surgery. At the same time, non-steroid anti-inflammatory drugs are used as medication.

If necessary, physiotherapy of liposuction areas is performed within the postoperative period.

In the combined liposuction method, in the postoperative period, compression dressings are used during four weeks after the end of the operation, wherein compression dressings are used around the clock during the first week after the end of the operation.

The combined liposuction method is as follows.

A preoperative examination of the patient is carried out, which includes taking patient's history, determining the patient's indications and contraindications for the operation, conducting laboratory tests for biochemical and general blood analysis, determining the blood group, Rh factor, Wasserman reaction, detecting antibodies to HIV, blood testing for hepatitis, doing an electrocardiogram of the patient, as well as examining the patient by a therapist. In this case, a biochemical blood test includes the determination of indicators for bilirubin, aminotransferase AST and ALT, sugar, creatinine, protein, electrolytes, and blood lipids. Operation planning is performed. For this purpose, the aesthetic condition of the lower third of the face and neck of the patient is preliminarily assessed. For this purpose, in particular, the thickness of the skin-fat fold is measured in the proposed areas of the operative field, for example, using a caliper, and based on the obtained values, the layer thickness and, accordingly, the volume of the adipose tissue to be removed is determined. Also, in particular, signs of age-related changes are assessed, such as the presence and degree of deformation of the contour of the lower jaw of the patient's face, the degree of turgor and skin elasticity, the presence and severity of skin wrinkles and folds, and the tone of the platysmus muscle. Based on the result of assessing the aesthetic condition of the lower third of the face and neck of the patient, one or more areas of the lower third of the face and neck from a number of such as the submental area of the neck, the lower jaw areas, the neck area from the submental area to the level of the cricoid cartilage, and the neck area from the submental area to the level of the jugular notch, are determined as the liposuction areas constituting the operative field. Accordingly, the contour boundaries of the operative field are determined. Depending on the location of the liposuction areas in the lower third of the face and neck, at least one operative approach point is determined. For example, in the case where it is planned to perform liposuction in the submental area of the neck and the lower jaw areas, it is preferable to determine single operative approach point in the area of the sub-mental fold. And in the case where liposuction is planned to be performed in the neck area from the submental area to the level of the cricoid cartilage or to the level of the jugular notch, two operative approach points are determined, wherein their location is determined under the corners of the lower jaw, by one operative approach point from each side of the neck. Contour boundaries of the operative field, as well as determined operative approach points are marked on the patient's body in areas of the lower third of the face and neck when the patient is standing. Areas of liposuction are photographed in several projections. The range is determined and the values of the Nd:YAG laser radiation power with a wavelength of 1064 nm are set, depending on which areas of the lower third of the face and neck of the patient were designated as liposuction areas and, in fact, constitute the operative field. So, in the case where the operative field is the submental area of the neck, the Nd:YAG laser radiation power with a wavelength of 1064 nm is set in the range from 8 W to 12 W, in the case where the operative field is the submental area of the neck and the lower jaw areas, the value of the Nd:YAG laser radiation power with a wavelength of 1064 nm is set in the range from 12 W to 14 W, in the case where the operative field consists of the submental area of the neck, the lower jaw areas, and the neck area from the submental area to the level of the cricoid cartilage, the value the Nd:YAG laser radiation power with a wavelength of 1064 nm is set in the range from 14 W to 15 W, in the case where the operative field consists of the submental area of the neck, the lower jaw areas, and the neck area from the submental area to the level of the jugular notch, the Nd:YAG laser radiation power value with a wavelength of 1064 nm is set in the range from 15 W to 16 W. It is preferable to take into account the result of assessing the aesthetic condition of the lower third of the face and neck of the patient when setting the value of the Nd:YAG laser radiation power with a wavelength of 1064 nm within a certain range. Therefore, if a large number of signs of age-related changes and/or a large degree of their severity are present, the power value of the aforementioned laser radiation is set as higher in a certain range of values thereof. Uniform infiltration anesthesia of the adipose tissue to be removed is performed. To do this, a tumescent solution is prepared consisting of 50 ml of a 1% solution of lidocaine hydrochloride, 1 ml of adrenaline, 12.5 ml of an 8.4% sodium bicarbonate solution and physiological saline in the form of a 0.9% aqueous NaCl solution in an amount up to 1000 ml. Transcutaneous punctures of skin are made along the contour boundaries of the operative field using standard syringes, and the tumescent solution is injected under pressure into the adipose tissue to be removed to provide local intracellular hyperhydration of adipocytes. At the same time, at least part of the transcutaneous skin punctures is located at all predetermined operative approach points, and the ratio of the volume of the tumescent solution to the volume of the adipose tissue to be infiltrated is provided from 1:1 to 3:1, respectively. After performing uniform infiltration anesthesia of the adipose tissue to be removed, tunnels are formed therein, if necessary. To do this, transcutaneous skin punctures at predetermined operative approach points are expanded with a blunt dilator and a cannula is inserted through them into the adipose tissue to be removed. The cannula is put forward by in and out movements within the entire volume of the adipose tissue to be removed, and thereby forming the tunnels. Therewith, the tunnels are formed close to each other and arranged, for example, in the form of a fan-shaped network. Whereby, in the case where it is planned to perform liposuction in the submental area of the neck and the lower jaw areas through single operative approach point located in the area of the submental fold, in and out movements of the cannula within the volume of the adipose tissue to be removed are performed by entering into the front surface of the lower jaw of the face. To perform the liposuction operation, an Nd:YAG laser radiation source with a wavelength of 1064 nm and a fiber optic light guide with a fiber thickness of 600 microns are used. The first end of the fiber optic light guide is connected optically to said laser radiation source. The second end of the fiber optic light guide is made with an emitting radiation surface. For this purpose, the external protective coating is put out from the end fiber section of the fiber optic light guide at the second end thereof. Also the possibility of inserting the second end of the fiber optic light guide into the liposuction area through transcutaneous skin punctures is provided. To do this, an optical cannula having a diameter of, for example, 1 mm is used. The second end of the fiber optic light guide is placed inside the optical cannula so that emitting radiation surface thereof protrudes from the optical cannula and thus is able to emit radiation outside the optical cannula. Transcutaneous punctures of skin are made at predetermined operative approach points and dilated with a blunt dilator, if this was not done at the previous stages of the operation. Through the optical cannula in which it is placed, the second end of the fiber optic light guide comprising a Nd:YAG laser radiation source with a wavelength of 1064 nm is inserted into the adipose tissue to be removed through expanded transcutaneous skin punctures at predetermined operative approach points. Nd:YAG laser radiation with a wavelength of 1064 nm in a pulsed mode with a frequency of 50 Hz, a pulse duration of 300 µs and a power of the predetermined value is supplied directly to the adipose tissue to be removed. In this case, the second end of the fiber optic light guide, through the optical cannula in which it is placed, is put forward by continuous in and out movements within the volume of the adipose tissue to be removed to ensure uniform destruction of the latter over the entire area and depth of the treated area of the operative field. As a rule, the speed of putting forward of the second end of the fiber optic light guide in the in and out manner within the volume of the adipose tissue to be removed is maintained at about 40-50 movements per minute. Whereby, in the case of liposuction in the submental area of the neck and the lower jaw areas through single operative approach point in the area of the submental fold, putting forward the second end of the fiber optic light guide in the in and out manner within the volume of the adipose tissue to be removed is performed by entering into the front surface of the lower jaw of the face. And in the event that tunnels have been previously formed in the adipose tissue to be removed, the second end of the fiber optic light guide is put forward by continuous in and out movements inside each tunnel formed within the volume of the adipose tissue to be removed. In this case, putting forward the second end of the fiber optic light guide in the in and out manner within the volume of the adipose tissue to be removed begins from lower layers of the adipose tissue with the subsequent transition to overlying layers thereof, which is especially preferred in the case of a large depth of the layer of the adipose tissue to be removed. At the end of the laser exposure of the adipose tissue to be removed, the second end of the fiber optic light guide, through the optical cannula in which it is placed, is removed from the transcutaneous puncture of the skin and the formed emulsified adipocyte fat detritus is removed from the liposuction area through an aspiration cannula using a negative pressure of 0.2-0.3 bar. After removal of the emulsified adipocyte fat detritus from the liposuction areas, the dermis therein is heated to 39-40° C. using Nd:YAG laser radiation with a wavelength of 1064 nm, which is supplied to the area of liposuction performed through the fiber optic light guide, by inserting the second end thereof into the area of liposuction performed through transcutaneous skin punctures at the operative approach points by means of an optical cannula in which it is placed. At the end of the liposuction operation, the surgical wounds are closed with aseptic dressings, compression dressings are applied to the liposuction areas, and the postoperative period is performed. During the postoperative period, surgical wounds are ligated using antiseptic solutions and water-soluble ointments with simultaneous administration of medications and antibacterial therapy with broad-spectrum antibiotics for 5-7 days after the operation. At the same time, non-steroid anti-inflammatory drugs are used as medication. If necessary, physiotherapy of liposuction areas is performed within the postoperative period. Compression dressings are used during four weeks after the end of the operation, while during the first week after the end of the operation, compression dressings are used around the clock.

The implementation of the proposed combined liposuction method of the lower third of the face and neck is illustrated by the following clinical examples.

Example 1. Female patient O., 30 years old, applied to the clinic "Sharm" in the Novosibirsk City with complaints of local excess of subcutaneous fat in the lower third of the face and neck. The use of lipolytic injections and other means of hardware cosmetology did not provide the patient with the desired results. A preoperative examination of the patient was carried out, which included collecting the patient's medical history, determining the patient's indications and contraindications for the operation, conducting laboratory tests for biochemical and general blood analysis, determining the blood group, Rh factor, Wasserman reaction, detecting antibodies to HIV, blood testing for hepatitis, doing an electrocardiogram of the patient, as well as examining the patient by a therapist. Thereby, biochemical blood test included the determination of indicators for bilirubin, aminotransferase AST and ALT, sugar, creatinine, protein, electrolytes, and blood lipids. Operation planning was performed. For this purpose, the aesthetic condition of the lower third of the patient's face and neck was preliminarily assessed, which assessment revealed a slight decrease in the elasticity of the skin of the neck, slight excess of subcutaneous fat in the chin area and a smoothed neck-chin angle, while the contours of the lower jaw were not changed. The thickness of the skin-fat fold was also measured with a caliper along the midline of the submental area, which was 10 mm. Based on the results of the assessment, the submental area of the patient's neck was designated as the liposuction area constituting the operative field. Accordingly, the contour boundaries of the operative field were determined and single point of operational approach was determined in the sub-mental fold. The contour boundaries of the operative field and the operative approach point were marked on the patient's body when she was standing. The liposuction area was photographed in five projections. Based on the fact that the operative field is the submental area of the neck, the Nd:YAG laser radiation power with a wavelength of 1064 nm was set in the range from 8 W to 12 W. Thereby, taking into account the fact that the revealed aesthetic shortcomings of the lower third of the patient's face and neck are not significantly expressed, the value of the laser radiation power of 8 W was set, which is the lowest value in this range. Then, uniform infiltration anesthesia of the adipose tissue to be removed was performed. To do this, a tumescent solution was prepared consisting of 50 ml of a 1% solution of lidocaine hydrochloride, 1 ml of adrenaline, 12.5 ml of an 8.4% sodium bicarbonate solution and physiological saline in the form of a 0.9% aqueous NaCl solution in an amount up to 1000 ml. Transcutaneous punctures of skin were made along the contour boundaries of the operative field using standard syringes, and the tumescent solution was injected under pressure into the adipose tissue to be removed to provide local intracellular hyperhydration of adipocytes. In this case, one of the transcutaneous skin punctures was located at the predetermined operative approach point in the sub-mental fold, and the ratio of the volume of the tumescent solution to the volume of the adipose tissue to be infiltrated was provided from 1:1 to 3:1, respectively. Accordingly, 150 ml of the tumescent solution were administered into the adipose tissue to be removed. 10-15 minutes after the start of the tumescent solution administering into the adipose tissue to be removed, a transcutaneous skin puncture at the predetermined operative approach point in the sub-mental fold was expanded with a blunt dilator to no more than 3 mm and a cannula was inserted through it into the adipose tissue to be removed. The cannula was put forward by in and out movements within the entire volume of the adipose tissue to be removed, and thus tunnels were formed. Thereby, the tunnels were formed close to each other, in the form of a fan-shaped network. To perform the liposuction operation, an Nd:YAG laser radiation source with a wavelength of 1064 nm and a fiber optic light guide with a fiber thickness of 600 microns were used, while the first end of the fiber optic light guide was connected optically to the said laser radiation source. And at the second end of the fiber optic light guide, the external protective coating was put out from the end section of the fiber, after which the second end of the fiber was placed inside the optical cannula having a diameter of 1 mm so that the uncoated section of the fiber protruded slightly from the optical cannula to allow the emitting radiation surface of the fiber to emit laser radiation outside the optical cannula. Through the expanded transcutaneous skin puncture located at the operative approach point in the sub-mental area, the second end of the fiber optic light guide was inserted into the infiltrated adipose tissue using the optical cannula in which it has been placed, and an Nd:YAG laser radiation source with a wavelength of 1064 nm was turned on. Nd:YAG laser radiation with a wavelength of 1064 nm was supplied directly to the adipose tissue to be removed in a pulsed mode with a frequency of 50 Hz, a pulse duration of 300 μs, and a power of 8 W. In this case, the second end of the fiber optic light guide through the optical cannula in which it is placed, was put forward by continuous in and out movements inside each tunnel formed within the volume of the adipose tissue to be removed, thereby starting from the lower layers of adipose tissue with subsequent transition to overlying layers thereof. Therefore, uniform destruction of adipose tissue was ensured over the entire area and depth of the treated liposuction area. At the same time, the speed of putting forward of the second end of the fiber optic light guide in the in and out manner within the volume of the adipose tissue to be removed was maintained at about 40-50 movements per minute. As a result of the laser exposure of adipose tissue, the total amount of energy spent was 2500 J. After the laser treatment of adipose tissue was completed, the second end of the fiber optic light guide was removed from the transcutaneous puncture through the optical cannula into which it was placed and the formed emulsified adipocyte fat detritus was removed from the liposuction area through an aspiration cannula using a negative pressure of bar. After removal of the emulsified adipocyte fat detritus from the liposuction area, the dermis therein was heated to 39-40° C. using Nd:YAG laser radiation with a wavelength of 1064 nm, which was supplied to the area of the liposuction performed through the fiber optic light guide, by inserting second end thereof into the area of the liposuction performed by means of an optical cannula in which it is placed through a transcutaneous puncture of the skin at the operative approach point. At the end of the liposuction operation, a non-absorbable suture thread Prolene 6-0 was sutured to the site of the transcutaneous puncture, which site then was closed with an aseptic dressing, a compression dressing was applied to the liposuction area, and the postoperative period was performed. In the postoperative period, the patient's surgical wounds were ligated using alcohol chlorhexine and water-soluble ointments, simultaneously with this, the patient was given antibacterial therapy with broad-spectrum antibiotics, and also the patient was taking non-steroid anti-inflammatory drugs during seven days after the operation. During the first seven days after surgery, the patient used compression dressings around the clock, and then only at night for twenty-one days. As a result of combined liposuction performed by the claimed method, 30 ml of fat detritus were removed at once, there was no damage to the surrounding tissue architecture, blood loss was minimal, the recovery period lasted four weeks, the maximum effect of "skin tightening" was obtained, thereby achieving high aesthetic effect. Control examination of the patient showed the thickness of the skin-fat fold along the midline of the submental area in the amount of 2 mm.

Example 2. Female patient L., 48 years old, applied to the clinic "Sharm" in Novosibirsk City with complaints of local excess of subcutaneous fat in the lower third of the face and neck. The patient had not visited cosmetologists before; she had not performed any therapy in this area. A preoperative examination of the patient was carried out, which included collecting the patient's medical history, determining the patient's indications and contraindications for the operation, conducting laboratory tests for biochemical and general blood analysis, determining the blood group, Rh factor, Wasserman reaction, detecting antibodies to HIV, blood testing for hepatitis, doing an electrocardiogram of the patient, as well as examining the patient by a therapist. In this case, a biochemical blood test included the determination of indicators for bilirubin, aminotransferase AST and ALT, sugar, creatinine, protein, electrolytes, and blood lipids. Operation planning was performed. For this purpose, the aesthetic condition of the lower third of the face and neck of the patient was preliminarily assessed, which assessment revealed a moderate decrease in the elasticity of the skin of the neck, ptosis of the tissues of the lower third of the face, and the resulting changes in the contour of the lower jaw, local excess of subcutaneous fat in the chin area and smoothed cervical-chin angle. The thickness of the skin-fat fold in the midline of the submental area, measured with a caliper, was 13 mm. Based on the results of the assessment, the submental area of the neck and the lower jaw areas of the patient were determined as the liposuction areas constituting the operative field. Accordingly, the contour boundaries of the operative field and one point of operative approach in the submental fold were determined. The contour boundaries of the operative field and the operative approach point were marked on the patient's body when she was standing. Areas of liposuction were photographed in five projections. Based on the fact that the operative field consists of the submental area of the neck and the lower jaw areas, the Nd:YAG laser radiation power with a wavelength of 1064 nm was set in the range from 12 W to 14 W, and the laser radiation power value was set to 12 W. Then, uniform infiltration anesthesia of the adipose tissue to be removed was performed. To do this, a tumescent solution was prepared consisting of 50 ml of a 1% solution of lidocaine hydrochloride, 1 ml of adrenaline, 12.5 ml of an 8.4% sodium bicarbonate solution and physiological saline in the form of a 0.9% aqueous NaCl solution in an amount up to 1000 ml. Transcutaneous skin punctures along the contour boundaries of the operative field were made using standard syringes, and the tumescent solution was injected under pressure into the adipose tissue to be removed to provide local intracellular hyperhydration of adipocytes. In this case, one of the transcutaneous skin punctures was located at the predetermined operative approach point in the sub-mental fold, and the ratio of the volume of the tumescent solution to the volume of the adipose tissue to be infiltrated was from 1:1 to 3:1, respectively. Accordingly, 200 ml of the tumescent solution were administered into the adipose tissue to be removed. 10-15 minutes after the start of the tumescent solution administering into the adipose tissue to be removed, the transcutaneous puncture of the skin at the predetermined operative approach point in the sub-mental fold was expanded with a blunt dilator to a size of no more than 3 mm and a cannula was inserted through it into the adipose tissue to be removed. The cannula was put forward by in and out movements within the entire volume of the adipose tissue to be removed, and thereby forming the tunnels. Thus, the tunnels were formed close to each other, in the form of a fan-shaped network, and by entering into the front surface of the lower jaw of the face. To perform the liposuction operation, an Nd:YAG laser radiation source with a wavelength of 1064 nm and a fiber optic light guide with a fiber thickness of 600 microns were used, while the first end of the fiber optic light guide was connected optically to the said laser radiation source. And at the second end of the fiber optic light guide, the external protective coating was put out from the end section of the fiber, after which the second end of the fiber optic light guide was placed inside an optical cannula having a diameter of 1 mm so that the uncoated section of the fiber protruded slightly from the optical cannula to allow the emitting radiation surface of the fiber to emit laser radiation outside the optical cannula. Through the expanded transcutaneous skin puncture located at the operative approach point in the sub-mental fold, the second end of the fiber optic light guide was inserted into the infiltrated adipose tissue using the optical cannula in which it has been placed, and the Nd:YAG laser radiation source with a wavelength of 1064 nm was turned on. Nd:YAG laser radiation with a wavelength of 1064 nm was supplied directly to the adipose tissue to be removed in a pulsed mode with a frequency of 50 Hz, a pulse duration of 300 µs, and a power of 12 W. In this case, the second end of the fiber optic light guide through the optical cannula in which it is placed, was put forward by continuous in and out movements inside each tunnel formed within the volume of the adipose tissue to be removed, thereby starting from the lower layers of adipose tissue with subsequent transition to overlying layers thereof. Thus, uniform destruction of adipose tissue was ensured over the entire area and depth of the treated area of the operative field. At the same time, the speed of putting forward of the second end of the fiber optic light guide in the in and out manner within the volume of the adipose tissue to be removed was maintained at about 40-50 movements per minute. As a result of laser exposure of the adipose tissue to be removed, the total amount of energy spent was 3000 J. After the laser irradiation of adipose tissue was completed, the second end of the fiber optic light guide was removed from the transcutaneous puncture through the optical cannula in which it has been placed, and the formed emulsified adipocyte fat detritus was removed from the liposuction areas through an aspiration cannula using a negative pressure of 0.2-0.3 bar. After removal of the emulsified adipocyte fat detritus from the liposuction areas, the dermis therein was heated to 39-40° C. using Nd:YAG laser radiation with a wavelength of 1064 nm, which was supplied to the areas of liposuction performed, also via the fiber optic light guide, by insertion of second end thereof into the area of liposuction performed using the optical cannula in which it has been placed through a transcutaneous puncture of the skin at the operative approach point. At the end of the liposuction operation, a non-absorbable suture thread Prolene 6-0 was sutured to the site of the transcutaneous puncture, which site then was closed with an aseptic dressing, a compression dressing was applied to the liposuction area, and the postoperative period was performed. In the postoperative period, the patient's surgical wounds were ligated using alcohol chlorhexine and water-soluble ointments, simultaneously the patient was given antibacterial therapy with broad-spectrum antibiotics for seven days after the operation, and also the patient was taking non-steroid anti-inflammatory drugs. During the first seven days after the operation, the patient used a compression dressing around the clock, and then only at night for twenty-one days. In the early postoperative period, the patient received physiotherapy of the areas of liposuction performed in the form of twelve ultrasound procedures with hydrocortisone. As a result of combined liposuction performed by the claimed method, 50 ml of fat detritus were removed at once, there was no damage to the surrounding tissue structures, blood loss was minimal, the recovery period lasted four weeks, the maximum effect of "skin tightening" was obtained, thereby achieving a high aesthetic effect. Control examination of the patient showed the thickness of the skin-fat folds along the midline of the submental area in the amount of 2 mm.

Example 3. Female patient P., 45 years old, applied to the clinic "Sharm" in Novosibirsk City with complaints of local excess of subcutaneous fat in the lower third of the face and neck. A preoperative examination of the patient was carried out, which included collecting the patient's medical history, determining the patient's indications and contraindications for the operation, conducting laboratory tests for biochemical and general blood analysis, determining the blood group, Rh factor, Wasserman reaction, detecting antibodies to HIV, blood testing for hepatitis, doing an electrocardiogram of the patient, as well as examining the patient by a therapist. In this case, a biochemical blood test included the determination of indicators for bilirubin, aminotransferase AST and ALT, sugar, creatinine, protein, electrolytes, and blood lipids. Operation planning was performed. For this purpose, the aesthetic condition of the lower third of the face and neck of the patient was preliminarily assessed, which assessment revealed flaws, pronounced changes in the contour of the lower jaw, local excess of subcutaneous fat in the chin area, smoothed cervical-chin angle, a decrease of skin elasticity and the tone of the platysmus muscle. Also the thickness of the skin-fat fold in the midline of the submental area was measured with a caliper, which was 18 mm. Based on the results of the assessment, the submental area of the neck, the lower jaw areas, and the neck area from the submental area to the level of cricoid cartilage were determined as the liposuction areas constituting the operative field. Accordingly, the contour boundaries of the operative field were determined and operative approach points were determined, one in the submental fold and two under the corners of the lower jaw, by one operative approach point from each side of the neck. The contour boundaries of the operative field and operative approach points were marked on the patient's body when she was standing. Areas of liposuction were photographed in five projections. Based on the fact that the operative field consists of the submental area of the neck, the lower jaw areas, and the neck area from the submental area to the level of cricoid cartilage, the Nd:YAG laser radiation power with a wavelength of 1064 nm was set in the range from 14 W to 15 W, and the laser radiation power value was set to 14 W. Then, uniform infiltration anesthesia of the adipose tissue to be removed was performed. To do this, a tumescent solution was prepared consisting of 50 ml of a 1% solution of lidocaine hydrochloride, 1 ml of adrenaline, 12.5 ml of an 8.4% sodium bicarbonate solution and physiological saline in the form of a 0.9% aqueous NaCl solution in an amount up to 1000 ml. Transcutaneous skin punctures were made along the contour boundaries of the operative field using standard syringes, and the tumescent solution was injected under pressure into the adipose tissue to be removed to provide local intracellular hyperhydration of adipocytes. In this case, three of the transcutaneous skin punctures were located at the predetermined operative approach points. One transcutaneous puncture in the sub-mental fold and two transcutaneous punctures under the corners of the lower jaw for each side of the neck, respectively, and the ratio of the volume of the tumescent solution to the volume of the adipose tissue to be infiltrated was from 1:1 to 3:1, respectively. Accordingly, 230 ml of the tumescent solution were administered into the adipose tissue to be removed. 10-15 minutes after the start of the tumescent solution administering into the adipose tissue to be removed, the transcutaneous skin punctures at the predetermined operative approach points in the sub-mental fold were expanded with a blunt dilator to a size of no more than 3 mm and a cannula was inserted through them into the adipose tissue to be removed. The cannula was put forward by in and out movements within the entire volume of the adipose tissue to be removed, and thus tunnels were formed. Thereby, the tunnels were formed close to each other, in the form of a fan-shaped network, accordingly to the operative approach points location, and by entering into the front surface of the lower jaw and to the neck up to the level of cricoid cartilage. To perform the liposuction operation, a Nd:YAG laser radiation source with a wavelength of 1064 nm and a fiber optic light guide with a fiber thickness of 600 microns were used, while the first end of the fiber optic light guide was connected optically to the said laser radiation source. The external protective coating was put out from the end section of the fiber at the second end of the fiber optic light guide, after which the second end of the fiber optic light guide was placed inside an optical cannula having a diameter of 1 mm so that the uncoated section of the fiber protruded slightly from the optical cannula to allow the emitting radiation surface of the fiber to emit laser radiation outside the optical cannula. Through the expanded transcutaneous skin punctures located at the operative approach points, the second end of the fiber optic light guide was inserted into the infiltrated adipose tissue using the optical cannula in which it has been placed, and the Nd:YAG laser radiation source with a wavelength of 1064 nm was turned on. Nd:YAG laser radiation with a wavelength of 1064 nm was supplied directly to the adipose tissue to be removed in a pulsed mode with a frequency of 50 Hz, a pulse duration of 300 µs, and a power of 14 W. In this case, the second end of the fiber optic light guide, through the optical cannula in which it is placed, was put forward by continuous in and out movements inside each tunnel formed within the volume of the adipose tissue to be removed, thereby starting from the lower layers of adipose tissue with subsequent transition to its overlying layers. Thus, uniform destruction of adipose tissue was ensured over the entire area and depth of the treated area of the operative field. At the same time, the speed of putting forward of the second end of the fiber optic light guide in the in and out manner within the volume of the adipose tissue to be removed was maintained at about movements per minute. As a result of laser exposure of the adipose tissue to be removed, the total amount of energy spent was 3500 J. After the laser irradiation of adipose tissue was completed, the second end of the fiber optic light guide was removed from the transcutaneous puncture through the optical cannula in which it has been placed, and the formed emulsified adipocyte fat detritus was removed from the liposuction areas through an aspiration cannula using a negative pressure of 0.2-0.3 bar. After removal of the emulsified adipocyte fat detritus from the liposuction areas, the dermis therein was heated to 39-40° C. using Nd:YAG laser radiation with a wavelength of 1064 nm, which was supplied to the area of liposuction performed, also via the fiber optic light guide, by insertion of second end thereof into the area of liposuction performed by means of the optical cannula in which it has been placed through a transcutaneous skin punctures at the operative approach points. At the end of the liposuction operation, a non-absorbable suture thread Prolene 6-0 was sutured to the sites of the transcutaneous punctures, which sites then were closed with an aseptic dressing, a compression dressing was applied to the liposuction area, and the postoperative period was performed. In the postoperative period, the patient's surgical wounds were ligated using alcohol chlorhexine and water-soluble ointments, simultaneously the patient was given antibacterial therapy with broad-spectrum antibiotics for seven days after the operation, and also the patient was taking non-steroid anti-inflammatory drugs. During the first seven days after surgery, the patient used a compression dressing around the clock, and then only at night for twenty-one days. In the early postoperative period, the patient received physiotherapy of the areas of liposuction performed in the form of twelve ultrasound procedures with hydrocortisone and twelve ultrasound procedures with the preparation based on the complex of collagenolytic proteases "Fermencol gel". As a result of combined liposuction performed by the claimed method, 60 ml of fat detritus were removed at once, there was no damage to the surrounding tissue structures, blood loss was minimal, the recovery period lasted four weeks, the maximum effect of "skin tightening" was obtained, thereby achieving a high aesthetic effect. Control examination of the patient showed the thickness of the skin-fat folds along the midline of the submental area in the amount of 3 mm.

Example 4. Female patient L., 58 years old, applied to the clinic "Sharm" in Novosibirsk City with complaints of local excess of subcutaneous fat in the lower third of the face and neck. A preoperative examination of the patient was carried out, which included collecting the patient's medical history, determining the patient's indications and contraindications for the operation, conducting laboratory tests for biochemical and general blood analysis, determining the blood group, Rh factor, Wasserman reaction, detecting antibodies to HIV, blood testing for hepatitis, doing an electrocardiogram of the patient, as well as examining the patient by a therapist. In this case, a biochemical blood test included the determination of indicators for bilirubin, aminotransferase AST and ALT, sugar, creatinine, protein, electrolytes, and blood lipids. Operation planning was performed. For this purpose, the aesthetic condition of the lower third of the face and neck of the patient was preliminarily assessed, which assessment revealed flaws and associated pronounced changes in the contour of the lower jaw, local excess of subcutaneous fat in the chin area, smoothed cervical-chin angle, loose skin with circular wrinkles, and decreased tone of the platysmus muscle. Also the thickness of the skin-fat fold in the midline of the submental area was measured with a caliper, which was 23 mm. Based on the results of the assessment, the submental area of the neck, the lower jaw areas, and the neck area from the submental area to the level of jugular notch were determined as the liposuction areas constituting the operative field. Accordingly, the contour boundaries of the operative field were determined and operative approach points were determined, one in the submental fold and two under the corners of the lower jaw, by one operative approach point from each side of the neck. The contour boundaries of the operative field and the operative approach points were marked on the patient's body when she was standing. The liposuction areas were photographed in five projections. Based on the fact that the operative field consists of the submental area of the neck, the lower jaw areas, and the neck area from the submental area to the level of jugular notch, the Nd:YAG laser radiation power with a wavelength of 1064 nm was set in the range from 15 W to 16 W, and the laser radiation power value was set to 16 W. Then, uniform infiltration anesthesia of the adipose tissue to be removed was performed. To do this, a tumescent solution was prepared consisting of 50 ml of a 1% solution of lidocaine hydrochloride, 1 ml of adrenaline, 12.5 ml of an 8.4% sodium bicarbonate solution and physiological saline in the form of a 0.9% aqueous NaCl solution in an amount up to 1000 ml. Transcutaneous skin punctures were made along the contour boundaries of the operative field using standard syringes, and the tumescent solution was injected under pressure into the adipose tissue to be removed to provide local intracellular hyperhydration of adipocytes. In this case, three of the transcutaneous skin punctures were located at the predetermined operative approach points. One transcutaneous puncture in the sub-mental fold, and two transcutaneous punctures under the corners of the lower jaw, accordingly, and the ratio of the volume of the tumescent solution to the volume of the adipose tissue to be infiltrated was from 1:1 to 3:1, respectively. Accordingly, 270 ml of the tumescent solution were administered into the adipose tissue to be removed. 10-15 minutes after the start of the tumescent solution administering into the adipose tissue to be removed, the transcutaneous skin punctures at the predetermined operative approach points in the sub-mental fold were expanded with a blunt dilator to a size of no more than 3 mm and a cannula was inserted through them into the adipose tissue to be removed. The cannula was put forward by in and out movements within the entire volume of the adipose tissue to be removed, and thus tunnels were formed. Thereby, the tunnels were formed close to each other, in the form of a fan-shaped network, and accordingly to the operative approach points location, and by entering into the front surface of the lower jaw and to the neck up to the level of jugular notch. To perform the liposuction operation, an Nd:YAG laser radiation source with a wavelength of 1064 nm and a fiber optic light guide with a fiber thickness of 600 microns were used, while the first end of the fiber optic light guide was connected optically to the said laser radiation source. The external protective coating was put out from the end section of the fiber at the second end of the fiber optic light guide, after which the second end of the fiber optic light guide was placed inside an optical cannula having a diameter of 1 mm so that the uncoated section of the fiber protruded slightly from the optical cannula to allow the emitting radiation surface of the fiber to emit laser radiation outside the optical cannula. Through the expanded transcutaneous skin punctures located at the operative approach points, the second end of the fiber optic light guide was inserted into the infiltrated adipose tissue using the optical cannula in which it has been placed, and the Nd:YAG laser radiation source with a wavelength of 1064 nm was turned on. Nd:YAG laser radiation with a wavelength of 1064 nm was supplied directly to the adipose tissue to be removed in a pulsed mode with a frequency of 50 Hz, a pulse duration of 300 μs, and a power of 16 W. In this case, the second end of the fiber optic light guide through the optical cannula in which it is placed, was put forward by continuous in and out movements inside each tunnel formed within the volume of the adipose tissue to be removed, thereby starting from the lower layers of adipose tissue with subsequent transition to overlying layers thereof. Thus, uniform destruction of adipose tissue was ensured over the entire area and depth of the treated areas of the operative field. At the same time, the speed of putting forward of the second end of the fiber optic light guide in the in and out manner within the volume of the adipose tissue to be removed was maintained at about 40-50 movements per minute. As a result of laser exposure of the adipose tissue to be removed, the total amount of energy spent was 4000 J. After the laser irradiation of adipose tissue was completed, the second end of the fiber optic light guide was removed from the transcutaneous punctures through the optical cannula in which it has been placed, and the formed emulsified adipocyte fat detritus was removed from the liposuction areas through an aspiration cannula using a negative pressure of 0.2-0.3 bar. After removal of the emulsified adipocyte fat detritus from the liposuction areas, the dermis therein was heated to 39-40° C. using Nd:YAG laser radiation with a wavelength of 1064 nm, which was supplied to the areas of liposuction performed, also via the fiber optic light guide, by insertion of second end thereof into the area of liposuction performed by means of the optical cannula in which it has been placed through a transcutaneous skin punctures at the operative approach points. At the end of the liposuction operation, a non-absorbable suture thread Prolene 6-0 was sutured to the sites of the transcutaneous punctures, which sites then were closed with an aseptic dressings, compression dressings were applied to the liposuction areas and the postoperative period was performed. In the postoperative period, the patient's surgical wounds were ligated using alcohol chlorhexine and water-soluble ointments, simultaneously the patient was given antibacterial therapy with broad-spectrum antibiotics for seven days after the operation, and also the patient was taking non-steroid anti-inflammatory drugs. During the first seven days after surgery, the patient used compression dressings around the clock, and then only at night for twenty-one days. In the early postoperative period, the patient received physiotherapy of the areas of liposuction performed in the form of twelve ultrasound procedures with hydrocortisone and twelve ultrasound procedures with the preparation based on the complex of collagenolytic proteases "Fermencol gel". As a result of combined liposuction performed by the claimed method, 80 ml of fat detritus were removed at once, there was no damage to the surrounding tissue structures, blood loss was minimal, the recovery period lasted four weeks, the maximum effect of "skin tightening" was obtained, thereby achieving a high aesthetic effect. Control examination of the patient showed the thickness of the skin-fat folds along the midline of the submental area in the amount of 3 mm.

What is claimed is:

1. A combined liposuction method, which method comprises carrying out a preoperative examination of the patient, planning an operation wherein one or more areas of the lower third of the face and neck of the patient from a number of such as the submental area of the neck, the lower jaw areas, the neck area from its submental area to the level of the cricoid cartilage and the neck area from its submental area to the level of the jugular notch, are determined as the liposuction areas constituting an operative field, wherein the contour boundaries of the operative field and at least one operative approach point are determined, performing uniform infiltration anesthesia of the adipose tissue to be removed in the liposuction areas, using an Nd:YAG laser radiation source with a wavelength of 1064 nm and a fiber optic light guide with a fiber thickness of 600 microns, wherein the first end of the fiber optic light guide is connected optically to the laser radiation source, and the second end of the fiber optic light guide is made with an emitting radiation surface and provides the possibility of insertion thereof into the adipose tissue to be removed through transcutaneous skin punctures, causing the destructive effect on the adipose tissue to be removed by Nd:YAG laser radiation with a wavelength of 1064 nm, which is supplied in a pulsed mode with a frequency of 50 Hz, with a pulse duration of 300 μs and a power of the predetermined value from the laser radiation source through the fiber optic light guide directly to the adipose tissue to be removed in the liposuction areas, for which purpose the second end of the fiber optic light guide is inserted into the adipose tissue to be removed through transcutaneous skin punctures at predetermined operative approach points and is continuously put forward by in and out movements within the volume of the adipose tissue to be removed to ensure uniform destruction of the adipose tissue over the entire area and depth of the treated area of liposuction, removal of the formed emulsified adipocyte fat detritus from the liposuction areas, at the end of the operation, surgical wounds are closed with aseptic dressings, compression dressings on the liposuction areas are applied, and the postoperative period is performed, while in the case where the operative field consists of the submental area of the neck, the value of the Nd:YAG laser radiation power with a wavelength of 1064 nm is set in the range from 8 W to 12 W, in the case where the operative field consists of the submental area of the neck and the lower jaw areas, the value of the Nd:YAG laser radiation power with a wavelength of 1064 nm is set in the range from 12 W to 14 W, in the case where the operative field consists of the submental area of the neck, the lower jaw areas, and the neck area from its submental area to the level of the cricoid cartilage, the Nd:YAG laser radiation power with a wavelength of 1064 nm is set in the range from 14 W to 15 W, in the case where the operative field consists of the submental area of the neck, the lower jaw areas, and the neck area from its submental area to the level of the jugular notch, the Nd:YAG laser radiation power with a wavelength of 1064 nm is set in the range from 15 W to 16 W, wherein after removal of the formed emulsified adipocyte fat detritus from the liposuction areas, the dermis is heated up to 39° C. by Nd:YAG laser radiation with a wavelength of 1064 nm, which is supplied from the laser radiation source to the field of liposuction through the fiber optic light guide, wherein for performing liposuction in the lower jaw areas, single operative approach point is determined in the area of the submental fold, and wherein the continuous in and out movements of the second end of the fiber optic light guide within the volume of the adipose tissue to be removed are performed by entering into the front surface of the lower jaw.

2. The combined liposuction method according to claim 1, wherein the preoperative examination of the patient includes collecting the patient's history, determining the patient's indications and contraindications for the operation, conducting laboratory tests for biochemical and general blood analysis, determining the blood group, Rh factor, Wasserman reaction, detecting antibodies to HIV, blood test for hepatitis, doing an electrocardiogram of the patient, as well as examining the patient by a therapist.

3. The combined liposuction method according to claim 2, wherein the biochemical analysis of blood includes determining indicators for bilirubin, aminotransferase AST and ALT, sugar, creatinine, protein, electrolytes, and blood lipids.

4. The combined liposuction method according to claim 1, wherein the planning of the operation includes photographing the liposuction areas in several projections.

5. The combined liposuction method according to claim 1, wherein the uniform infiltration anesthesia of the adipose tissue to be removed is performed by administering the infiltrating anesthetic liquid under pressure into adipose tissue through transcutaneous skin punctures to provide local intracellular hyperhydration of adipocytes.

6. The combined liposuction method according to claim 5, wherein the transcutaneous skin punctures are made along the contour boundaries of the operative field, wherein at least a portion of the transcutaneous skin punctures are located at all predetermined operative access points.

7. The combined liposuction method according to claim 5, wherein the infiltrating anesthetic liquid is administered into the adipose tissue to be removed using standard syringes.

8. The combined liposuction method according to claim 5, wherein a tumescent solution is used as an infiltrating anesthetic liquid.

9. The combined liposuction method according to claim 8, wherein the tumescent solution contains 50 ml of a 1% solution of lidocaine hydrochloride, 1 ml of adrenaline, 12.5 ml of an 8.4% sodium bicarbonate solution and physiological saline in the form of a 0.9% aqueous NaCl solution in an amount of up to 1000 ml.

10. The combined liposuction method according to claim 9, wherein the ratio of the volume of the tumescent solution to the volume of adipose tissue to be infiltrated is from 1:1 to 3:1, respectively.

11. The combined liposuction method according to claim 1, wherein in order to enable the second end of the fiber optic light guide to be inserted into the adipose tissue to be removed through transcutaneous skin punctures, an optical cannula is used, while the second end of the fiber optic light guide is placed inside the cannula so that the emitting radiation surface thereof is able to emit radiation outside the optical cannula.

12. The combined liposuction method according to claim 1, wherein for performing liposuction in the neck area from its submental area to the level of the cricoid cartilage or to the level of the jugular notch, two operative approach points are determined, and location thereof is defined by one point under the corners of the lower jaw from each side of the neck.

13. The combined liposuction method according to claim 1, wherein after performing uniform infiltration anesthesia of the adipose tissue to be removed and before causing the destructive effect on the adipose tissue to be removed by Nd:YAG laser radiation with a wavelength of 1064 nm, tunnels are formed in the adipose tissue to be removed, for which purpose a cannula is inserted into the adipose tissue to be removed through transcutaneous skin punctures at the predetermined operative approach points, and then the cannula is put forward by in and out movements within the entire volume of the adipose tissue to be removed, wherein the tunnels are formed close to each other, and after insertion into the adipose tissue the second end of the fiber optic light guide, the latter is put forward by continuous in and out movements inside each tunnel formed within the volume of the adipose tissue to be removed.

14. The combined liposuction method according to claim 13, wherein the tunnels are formed in the form of a fan-shaped network.

15. The combined liposuction method according to claim 1, wherein the transcutaneous skin punctures are expanded with a blunt dilator for insertion of the fiber optic light guide therein.

16. The combined liposuction method according to claim 13, wherein the transcutaneous skin punctures are expanded with a blunt dilator for inserting the cannula therein.

17. The combined liposuction method according to claim 1, wherein when causing the destructive effect on the adipose tissue to be removed, the second end of the fiber optic light guide is put forward by continuous in and out movements within the volume of the adipose tissue to be removed, starting from lower layers of adipose tissue and subsequently transitioning to overlying layers thereof.

18. The combined liposuction method according to claim 1, wherein the removal of the formed emulsified adipocyte fat detritus from the liposuction areas is performed through an aspiration cannula.

19. The combined liposuction method according to claim 1, wherein the removal of the formed emulsified adipocyte fat detritus from the liposuction areas is performed using a negative pressure of 0.2-0.3 bar.

20. The combined liposuction method according to claim 1, wherein during the postoperative period, surgical wounds are ligated using antiseptic solutions and water-soluble ointments with simultaneous administering medications and antibacterial therapy with broad-spectrum antibiotics for 5-7 days after surgery.

21. The combined liposuction method according to claim 20, wherein non-steroid anti-inflammatory drugs are used as medication.

22. The combined liposuction method according to claim 1, wherein physiotherapy of the liposuction areas is performed within the postoperative period.

23. The combined liposuction method according to claim 1, wherein during the postoperative period, compression dressings are used during four weeks after the end of the operation, wherein compression dressings are used around the clock during the first week after the end of the operation.

* * * * *